(12) United States Patent
Pham et al.

(10) Patent No.: US 11,554,034 B2
(45) Date of Patent: Jan. 17, 2023

(54) METHOD AND ASSEMBLY FOR SECURING AN IMPLANTABLE MEDICAL DEVICE ON A DELIVERY SYSTEM

(71) Applicant: VENUS MEDTECH (HANGZHOU), INC., Zhejiang (CN)

(72) Inventors: Trinh Van Pham, Westminster, CA (US); Ashley Rachel Zeng, Irvine, CA (US)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 193 days.

(21) Appl. No.: 17/064,032

(22) Filed: Oct. 6, 2020

(65) Prior Publication Data

US 2022/0104956 A1 Apr. 7, 2022

(51) Int. Cl.
*A61F 2/958* (2013.01)
*A61F 2/95* (2013.01)
*A61F 2/966* (2013.01)

(52) U.S. Cl.
CPC ............ *A61F 2/958* (2013.01); *A61F 2/9522* (2020.05); *A61F 2/9662* (2020.05); *A61F 2002/9511* (2013.01); *A61F 2002/9583* (2013.01); *A61F 2002/9665* (2013.01)

(58) Field of Classification Search
CPC ...... A61F 2/958; A61F 2/9522; A61F 2/9662; A61F 2002/9511; A61F 2002/9583; A61F 2002/9665
See application file for complete search history.

(56) References Cited

U.S. PATENT DOCUMENTS

| | | |
|---|---|---|
| 7,198,636 B2 | 4/2007 | Cully et al. |
| 7,235,093 B2 | 6/2007 | Gregorich |
| 8,834,550 B2 | 9/2014 | Leanna et al. |
| 9,248,037 B2 | 2/2016 | Roeder et al. |
| 10,258,490 B2 | 4/2019 | Baxter et al. |
| 10,463,517 B2 | 11/2019 | Bradway et al. |
| 10,500,079 B2 | 12/2019 | Shrum et al. |
| 2010/0036360 A1* | 2/2010 | Herbowy ............ A61F 2/07 600/300 |
| 2018/0207010 A1 | 7/2018 | Kheradvar et al. |
| 2020/0008941 A1 | 1/2020 | Stappenbeck et al. |
| 2020/0146823 A1 | 5/2020 | Alon et al. |
| 2020/0188149 A1 | 6/2020 | Amos et al. |

* cited by examiner

*Primary Examiner* — Thomas McEvoy
(74) *Attorney, Agent, or Firm* — Raymond Sun

(57) ABSTRACT

A method and an assembly for securing a crimped medical device over a deflated balloon of a balloon catheter is provided. The medical device is positioned in its expanded state over the deflated balloon of the balloon catheter, and is then crimped over the deflated balloon. First and second eyelets of first and second strings, respectively, are then threaded through first and second rings, respectively, that are provided on the medical device. Next, a locking wire is advanced through a lumen defined between the sheath and the catheter body to exit the distal end of the sheath, and then advanced through the first and second eyelets and into the distal tip of the balloon catheter. The sheath is then advanced over the crimped medical device to the distal tip to completely cover the crimped medical device.

8 Claims, 9 Drawing Sheets

METHOD AND ASSEMBLY FOR SECURING AN IMPLANTABLE MEDICAL DEVICE ON A DELIVERY SYSTEM

BACKGROUND OF THE INVENTION

1. Field of the Invention

The present invention relates to the delivery of implantable devices into the human body, and in particular, to a method and an assembly for securing an implantable medical device to a delivery system for delivery to a treatment location, and for deployment of the implant at the treatment location.

2. Description of the Prior Art

Non-invasive deployment of certain medical devices has become the routine method for treating certain medical conditions. For example, stents and prosthetic heart valves are now delivered to treatment locations inside blood vessels and inside the heart via a transcatheter procedure that avoids invasive surgery.

To facilitate delivery to desired treatment locations, for certain procedures, the medical device (e.g., stents and prosthetic heart valves) is crimped on a deflated balloon catheter, and then threaded through an introducer or a sheath which is inserted into the vasculature to the targeted location. The medical device is then expanded by the underlying balloon to its intended size and secured at the desired treatment location. The balloon is then deflated and the balloon catheter is withdrawn.

The securing of the medical device on the balloon is normally accomplished by using friction, with shoulders provided on balloon catheter to block the medical device from moving during the insertion and delivery. During the balloon inflation, the balloon is normally first inflated at both ends thereof, so as to serve as a blockage to prevent the expanding medical device from moving laterally on the balloon.

While the current crimping and deployment of devices tend to be effective for most procedures, there can be some issues with the balloon expandable medical devices in certain situations. First, the crimped medical devices are exposed to the surrounding environment (e.g., the introducing sheath, blood vessels, etc.), which may cause the medical device to experience movement during insertion. When crossing the aortic arch, the exposed medical device tends to flare at its distal end on the outer surface, which can be a hazard to the artery. Second, the shoulders used in securing the medical device on the balloon can hold the medical device in place but carries a risk of piercing the balloon, as the medical device tends to move and presses against the shoulders.

Thus, there remains a need for a method and an assembly for securing an implantable medical device to a delivery system for delivery to a treatment location, and for deployment of the implant at the treatment location, in a manner which avoids the drawbacks mentioned above.

SUMMARY OF THE DISCLOSURE

In order to accomplish the objects of the present invention, there is provided a method and an assembly for securing a crimped medical device over a deflated balloon of a balloon catheter. A medical device is provided having a tubular device body that has a first end and a second end, with a first ring provided at the first end and a second ring provided at the second end. A balloon catheter is also provided having a catheter body that has a distal tip, and a balloon provided adjacent to, and proximal to, the distal tip. The balloon catheter further includes a first string secured to the balloon catheter at a position adjacent the distal end of the balloon and having a first eyelet, and a second string secured to the balloon catheter at a position adjacent the proximal end of the balloon and having a second eyelet. A sheath is provided for sliding movement over the catheter body and the balloon.

According to the method of the present invention, the medical device is positioned in its expanded state over the deflated balloon, and is then crimped over the deflated balloon. The first and second eyelets of the first and second strings, respectively, are then threaded through the first and second rings, respectively. Next, a locking wire is advanced through a lumen defined between the sheath and the catheter body to exit the distal end of the sheath, and then advanced through the first and second eyelets and into the distal tip. The sheath is then advanced over the crimped medical device to the distal tip to completely cover the crimped medical device.

The present invention provides a method and an assembly for effectively securing an implantable medical device to a delivery system for delivery to a treatment location, and for deployment of the implant at the treatment location, in a manner such that the medical device experiences minimal to no movement in its crimped position over the balloon. In addition, providing the rings at the opposing ends of the medical device, and using the rings to receive a locking wire that is threaded through these rings, prevents flaring of the ends of the medical device, thereby minimizing the risk of piercing the balloon.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1A:
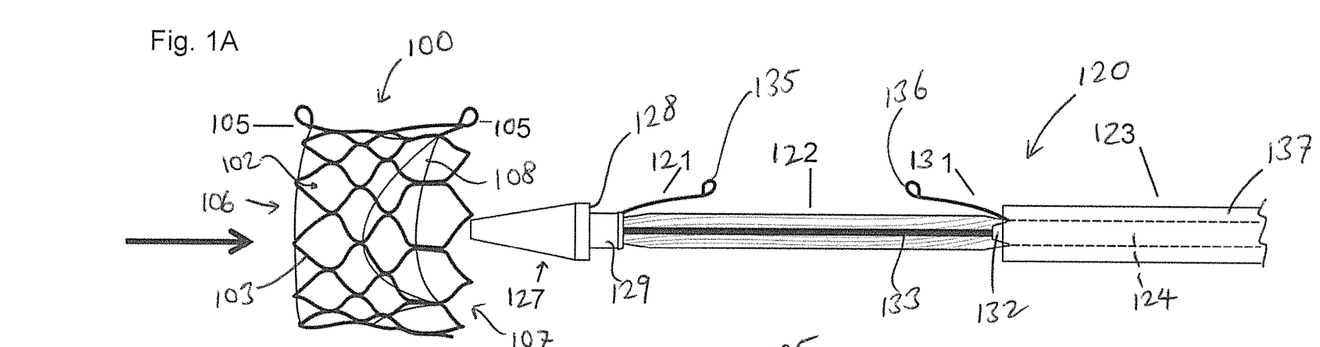
FIG. 1A is an exploded side view illustrating a medical device and a balloon catheter according to one embodiment of the present invention.

FIG. 1A is an exploded side view illustrating a medical device 100 and a balloon catheter 120 according to one embodiment of the present invention. The medical device 100 can be any medical device that is intended to be implanted into the human body, such as a stent, transcatheter heart valve, stent-graft assembly, closure device, and plug, among others. The drawings in the present invention are illustrated in connection with a transcatheter heart valve assembly 104 which can an expandable stent, or a stent-frame for use with a transcatheter heart valve. The stent heart valve assembly 104 can have a generally cylindrical stent body that has a plurality of cells 102 defined by struts 103. The stent body can be woven from a single wire or multiple wires, or laser cut from a metal (e.g., nickel-titanium) tube. The assembly 104 has a distal end 106 and a proximal end 107, a plurality of leaflets 108 secured inside the lumen of the stent body, and has at least one ring 105 provided at each of the distal end 106 and the proximal end 107. Other details for the heart valve assembly 104 are well-known to those skilled in the art and shall not be expanded upon herein.

The balloon catheter 120 has a catheter body 124 that has a distal tip 127, and a balloon 122 provided adjacent to, and proximal to, the distal tip 127. A capsule or sheath 123 is provided for sliding movement over the catheter body 124 and the balloon 122. The distal tip 127 can have a tapered configuration from its proximal end 128 to its distal-most end, and a cylindrical connector 129 having a smaller diameter than that of the proximal end 128 can be provided at the proximal end 128 and extend in the proximal direction. The distal end of the balloon 122 is secured to the proximal end surface of the connector 129, and the proximal end of the balloon is secured to the distal end 132 of the catheter body 124. A central tubing 133 extends through the central lumen of the catheter body 124 and its proximal end is connected to a handle assembly (not shown), and the distal end of central tubing 133 is connected to the connector 129, and extends through the interior of the balloon 122.

The construction of the balloon catheter 120 as described hereinabove is similar to that of any conventional balloon catheter having a distal tip and a balloon positioned adjacent the distal tip. The present invention adds two adjustment strings 121 and 131 that are used to releasably secure the medical device 100 (i.e., the heart valve assembly 104 in this embodiment) over the position of the balloon 122. Specifically, the string 121 is secured to the connector 129 and has an eyelet 135, and the string 121 extends in a proximal direction from the connector 129 over the balloon 122. Similarly, the string 131 is secured to the distal end 132 of the catheter body 124 and has an eyelet 136, and the string 131 extends in a distal direction from the distal end 132 over the balloon 122.

The sheath 123 has a proximal end (not shown) that is operatively connected to the handle assembly, and is adapted for slidable movement over the catheter body 124 as is known in the art.

The catheter body 124 can be made of Pebax, PTFE, Nylon, or any other known material that is used for catheter bodies; the sheath 123 can be made of Pebax, PTFE, Nylon or any other known material that is used for similar slidable sheaths; and the strings 121 and 131 can be made of polypropylene suture, braided PET suture, PTFE sutures, or any conventional suture. The balloon 122 can be made of any conventional balloon material, such as Nylon, and Pebax™. The rings 105 can be made of metal, such as the same material as the stent body.

Figure 1B:
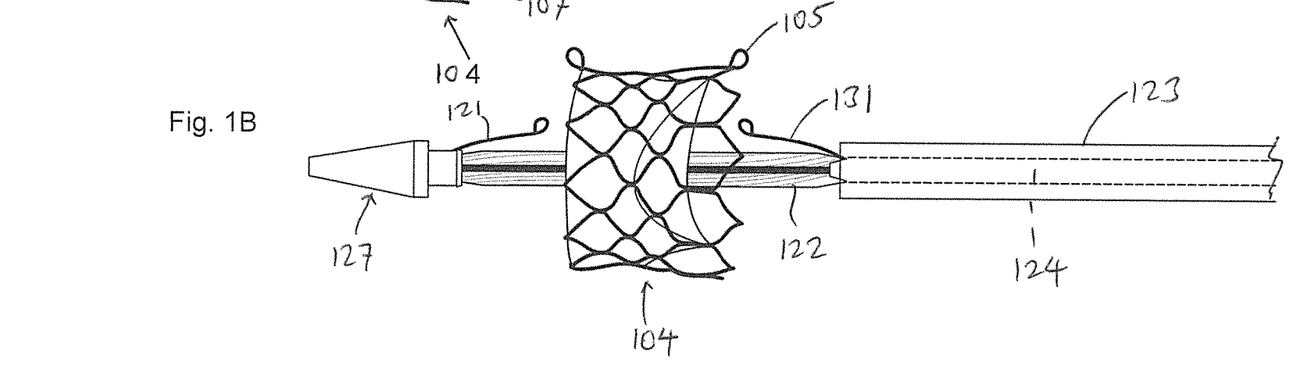
FIG. 1B is a side view that illustrates how the medical device in FIG. 1A is positioned to surround the balloon of the balloon catheter.
Figure 2:
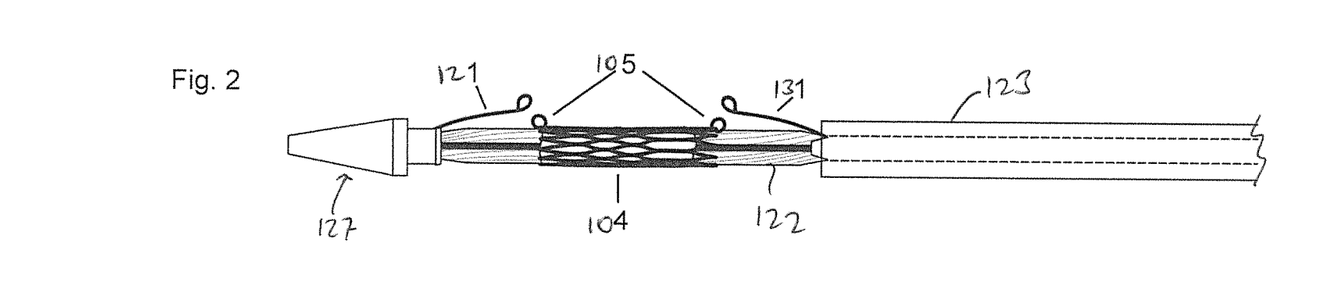
FIG. 2 illustrates how the medical device in FIG. 1A is crimped over the balloon of the balloon catheter.

FIG. 1A shows the heart valve assembly 104 being advanced over the balloon 122. The heart valve assembly 104 is in its expanded state and the balloon 122 is deflated. FIG. 1B shows the heart valve assembly 104 positioned directly over the deflated balloon 122, and FIG. 2 shows the heart valve assembly 104 crimped over the balloon 122.

Figures 3A, 3B:
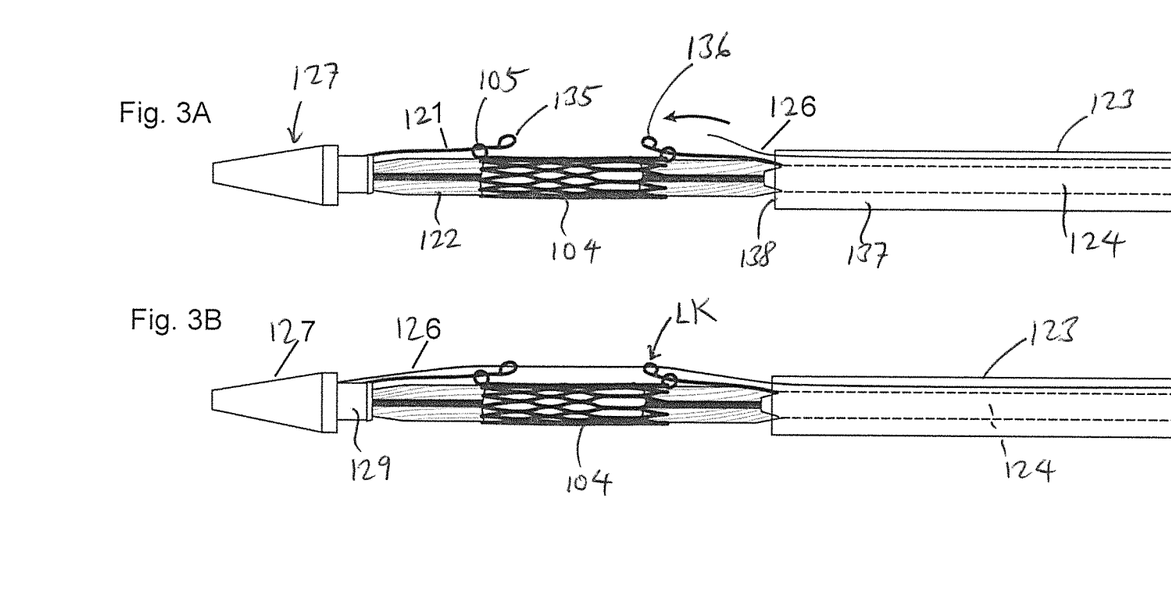
FIG. 3A illustrates how strings are extended through the rings provided on the ends of the medical device.
FIG. 3B illustrates how a locking wire is extended from the delivery sheath through eyelets on the strings and into a distal tip.

Referring to FIG. 3A, the eyelets 135 and 136 of the strings 121 and 131 are threaded through the rings 105 at the distal end 106 and the proximal end 107, respectively, of the heart valve assembly 104. This can be done manually by a person during the assembly process using specialized tools. Once this is completed, a locking wire 126 is advanced through a locking wire lumen 137 that is defined between the sheath 123 and the catheter body 124, and exits the distal end 138 of the sheath 123. The locking wire 126 can be made of 304 or 316 stainless steel with a PTFE coating.

Next, as shown in FIG. 3B, the locking wire 126 is advanced through the eyelets 135 and 136 and into a hole (not shown) inside the distal tip 127. The location LK in FIG. 3B illustrates a locking knot where the locking wire 126 passes through an eyelet 135/136 after the eyelet 135/136 has been threaded through the rings 105. The hole inside the distal tip 127 should have a certain depth so that the locking wire 126 can be securely locked inside the distal tip 127. With this assembly and construction, the heart valve assembly 104 is securely restrained over the balloon 122 from any lateral movement, with the restraint provided by the strings 121 and 132 and the locking wire 126.

Figure 4:
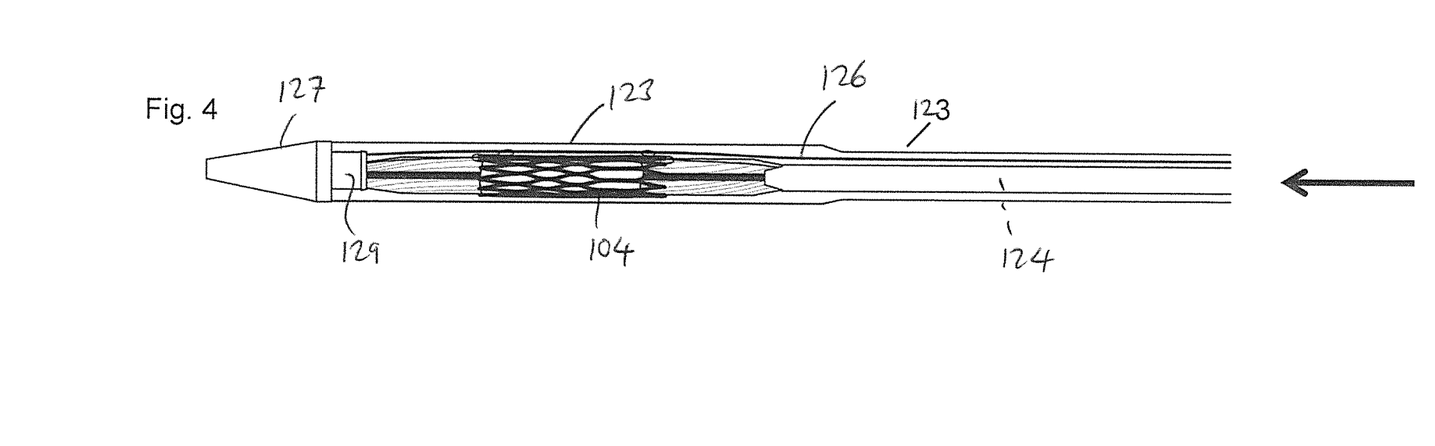
FIG. 4 illustrates the delivery sheath advanced over the medical device.

In the next step, the capsule or sheath 123 is advanced to the distal tip 127 to completely cover the crimped heart valve assembly 104 and the connector 129. The complete assembly (sheath 123 covering balloon catheter 120 with the heart valve assembly 104 carried over the balloon 122) is then advanced to the treatment location where the heart valve assembly 104 is to be implanted. The heart valve assembly 104 is securely restrained over the balloon 122 from any lateral movement during this delivery and advancement.

Figure 5:
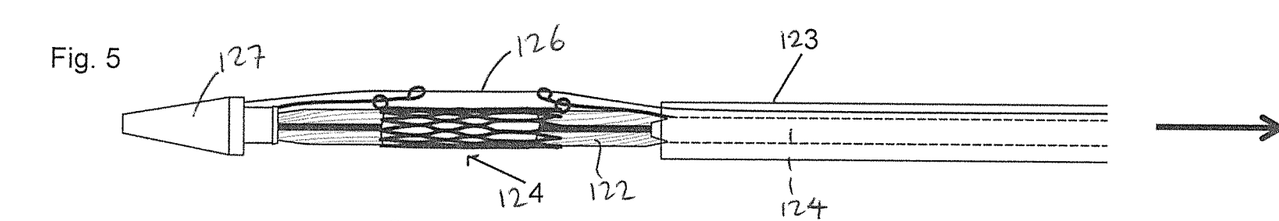
FIG. 5 illustrates the withdrawal of the delivery sheath to uncover the medical device.
Figure 6:
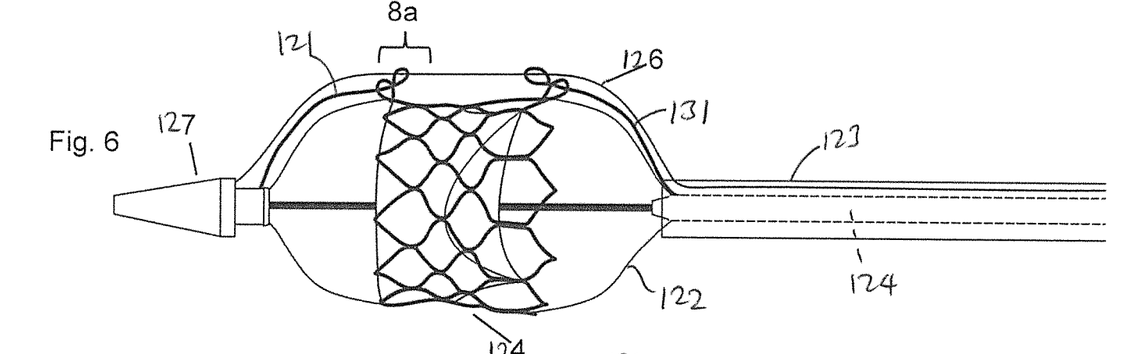
FIG. 6 illustrates the expansion of the balloon to expand the medical device.

FIGS. 5-9 illustrate the release and expansion of the heart valve assembly 104 at the treatment location, and the withdrawal of the balloon catheter 120. First, since the medical device 100 is a heart valve assembly 104, the treatment location is the annulus where the native heart valve (either aortic or mitral) is located. In FIG. 5, the sheath 123 is withdrawn to uncover or expose the heart valve assembly 104. Next, in FIG. 6, the balloon 122 is expanded, and the area 8a shows the interaction between the string eyelets 135/136, the locking wire 126, and the rings 105. During the steps illustrated in FIGS. 5 and 6, the locking wire 126 and the strings 121 and 131 restrain the heart valve assembly 104 from movement.

Figure 7:
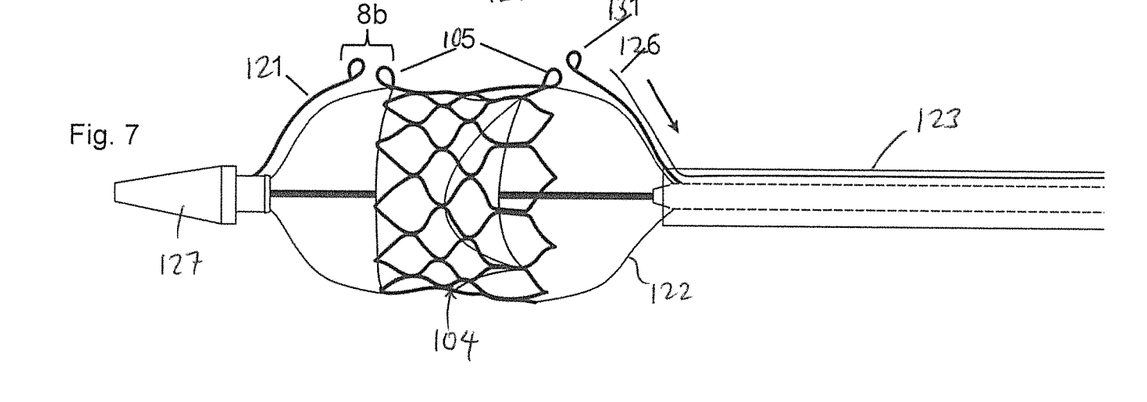
FIG. 7 illustrates the withdrawal of the locking wire from the eyelets and into the delivery sheath.
Figure 8:
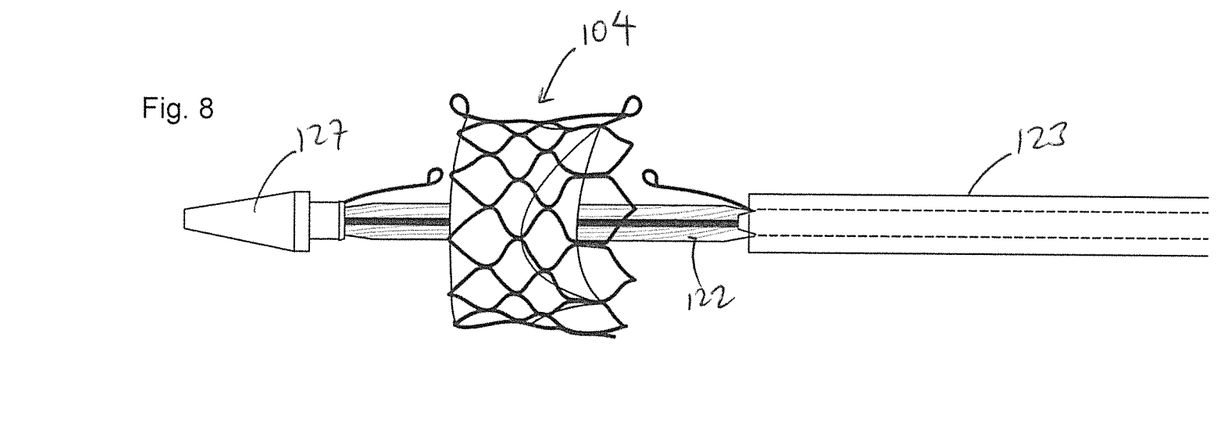
FIG. 8 illustrates the deflation of the balloon.
Figure 9:
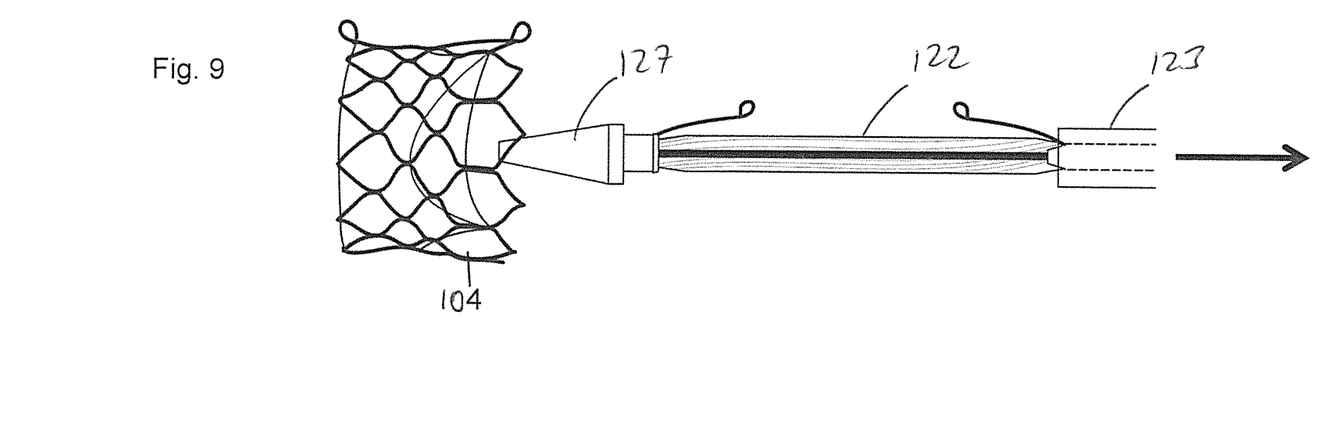
FIG. 9 illustrates the withdrawal of the balloon catheter.

Referring to FIG. 7, when the heart valve assembly 104 is fully expanded, the locking wire 126 is withdrawn and the eyelets 135/136 will automatically and completely disengage from their corresponding rings 105. The area 8b illustrates the disengagement between the eyelets 135/136 and their rings 105. Next, in FIG. 8, the locking wire 126 is completely withdrawn and the balloon 122 is deflated. Finally, in FIG. 9, the balloon catheter 120 is withdrawn.

Figure 10:
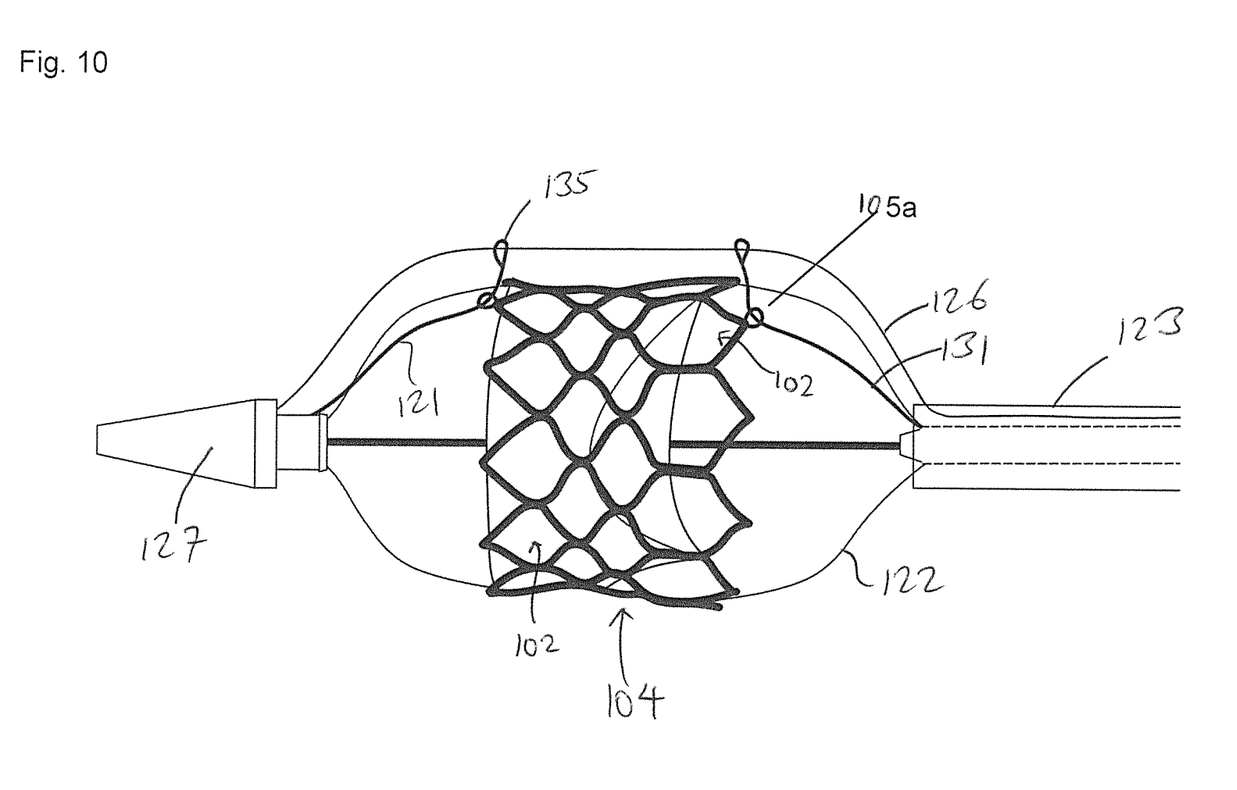
FIGS. 10-12 illustrate different embodiments for the medical device in FIG. 1A that can be used with the balloon catheter of FIG. 1A and the method of FIGS. 1A-9.
Figure 11:
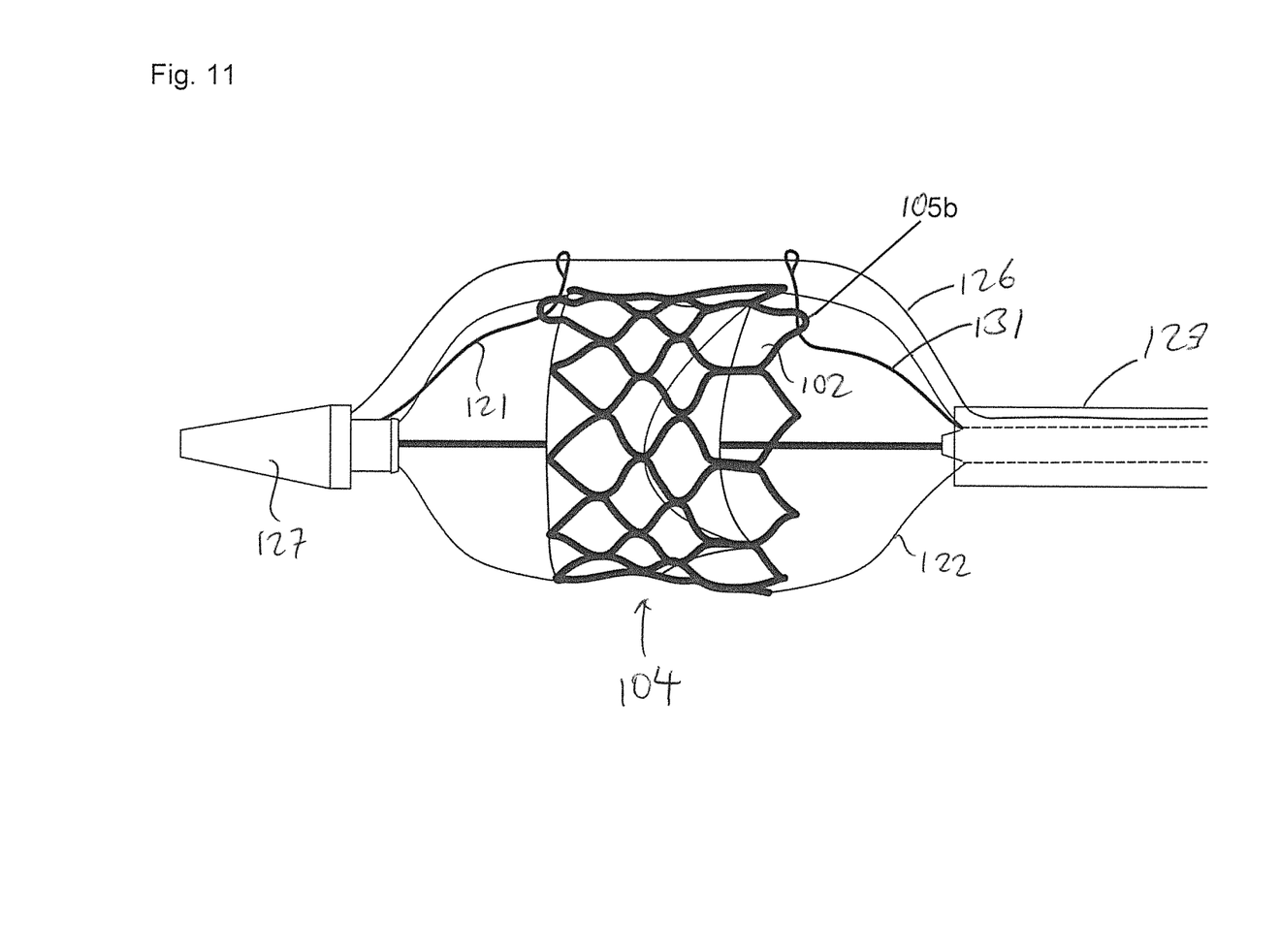
Figure 12:
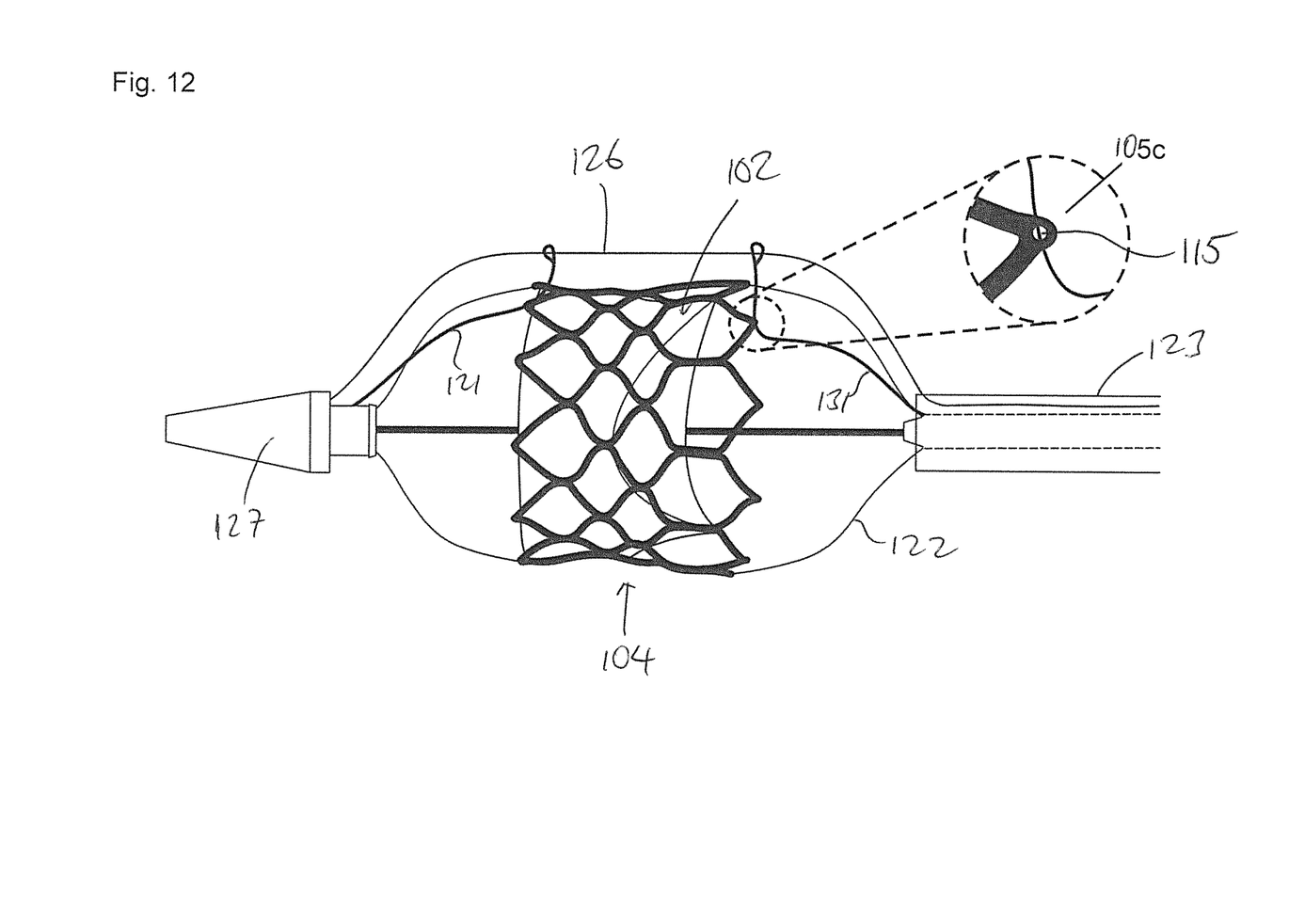

FIGS. 10-12 illustrate different embodiments showing alternatives for the rings 105. In FIG. 10, the rings 105a are independent rings and they can be made of the same or different materials from the material of the struts 103. During the assembly of the heart valve assembly 104, the rings 105a are manually attached to corresponding struts 103. The rings 105a can be made of any conventional suture material (e.g., polypropylene, PTFE) or the same material as the struts 103.

FIG. 11 shows another alternative where the rings 105 are replaced by rounded or enlarged tips 105b (also referred to as "strut loops") of the cells 102, with the strings 121, 131 adapted to extend into the space defined by the rounded tips 105b in the same manner in which they would extend into the openings of the rings 105.

In yet another embodiment, FIG. 12 shows holes 115 provided in the apices 105c of the cells 102, with the strings 121, 131 adapted to extend into the holes 115 in the same manner in which they would extend into the openings of the rings 105.

FIGS. 13A-14B illustrate another embodiment of the present invention where a connecting wire 140 connects the strings 121, 131 to create adjustable locking knots. The central tubing 133 has a first central lumen 141 and a second lumen 142 that is offset from the first central lumen 141. Openings 143 and 144 are provided in spaced apart manner communicating the second lumen 142 with the exterior of the central tubing 133, with the string 121 extending through the opening 144 and the string 131 extending through the opening 143. The connecting wire 140 extends through the second lumen 142 between the two openings 143 and 144, such that a first end of the connecting wire 140 connects to the string 121, and the opposing second end of the connecting wire 140 connects to the string 131. See FIG. 13B. The connecting wire 140 can be an extension of the same string 131 that exits through the opening 143.

Figure 13A:
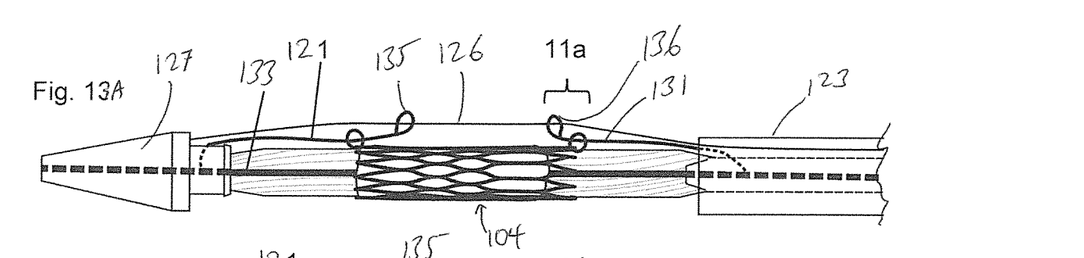
FIG. 13A is a side view illustrating a medical device crimped over a balloon catheter according to another embodiment of the present invention.
Figure 13B:
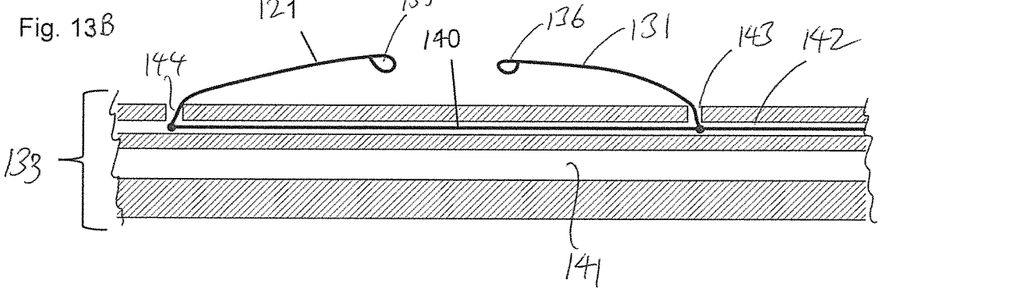
FIG. 13B is a cross-sectional side view of FIG. 13A shown without the medical device.

When the connecting wire 140 is advanced towards the distal tip 127, the strings 121 and 131 become exposed for a greater length, which provides enough room or space for the eyelets 135/136 to be threaded through the corresponding rings 105.

For example, FIGS. 13A and 13B illustrate the connecting wire 140 in a relaxed state, so that the exposed parts (i.e., outside the lumen 142) of the strings 121 and 131 can be longer. As shown in FIG. 13A, when the exposed parts of the strings 121 and 131 are longer, the crimped heart valve assembly 104 has room to slide back and forth (see the adjustable locking knot 11a) and is therefore poorly secured.

Figure 14A:
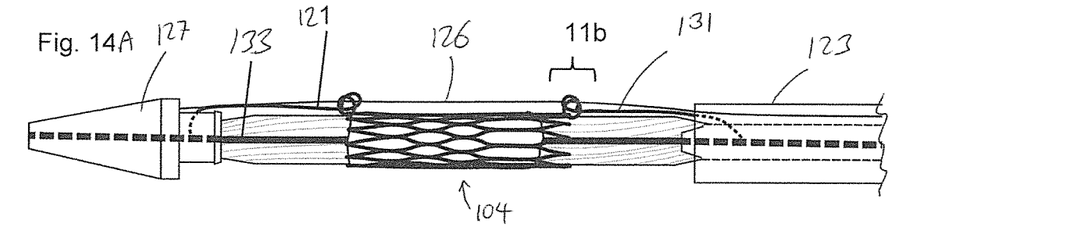
FIG. 14A is a side view of FIG. 13A showing the adjustment wire pulled taut.
Figure 14B:
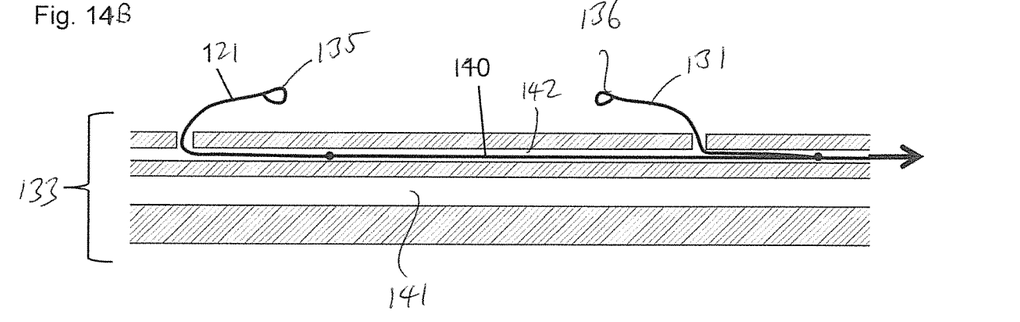
FIG. 14B is a cross-sectional side view of FIG. 14A shown without the medical device.

However, in FIG. 14B, when the connecting wire 140 is pulled taut, the strings 121 and 131 are also pulled along, so that the exposed parts of the strings 121 and 131 become shorter. As shown in FIG. 14A, the eyelets 135 and 136 at the ends of the strings 121 and 131, respectively, are aligned with the rings 105 on the heart valve assembly 104 (see the adjustable locking knot 11b), so that the heart valve assembly 104 is tightly secured.

Figure 15A:
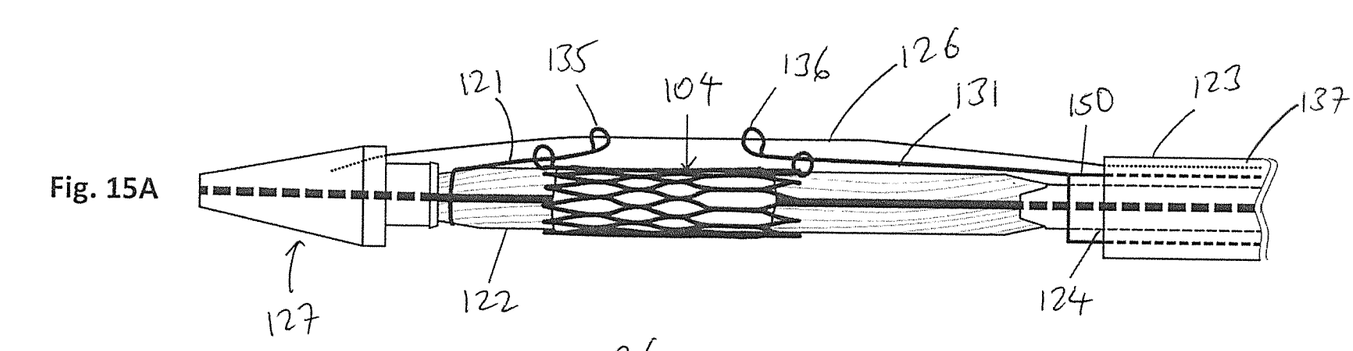
FIG. 15A is a side view of FIG. 13A showing the locking wire connected to a middle sheath.
Figure 15B:
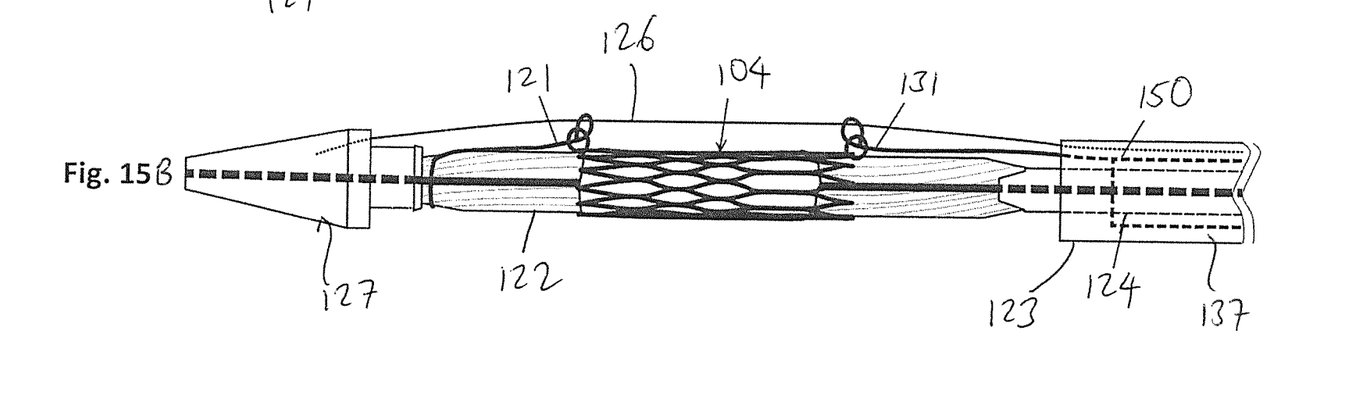
FIG. 15B is a side view of FIG. 15A showing the locking wire pulled taut by the middle sheath.

FIGS. 15A and 15B illustrate another embodiment of the present invention, where a middle sheath 150 is provided in the lumen 137, surrounding the catheter body 124. The proximal string 131 can be secured to the distal end of the middle sheath 150, and the distal string 121 and can be secured directly to, or adjacent to, the connector 129. In FIG. 15A, the middle sheath 150 is advanced in a distal direction towards the balloon 122, with the distal end of the middle sheath 150 exposed by the sheath 123, so that the eyelets 135 and 136 can be extended through and past the corresponding rings 105. In FIG. 15B, the middle sheath 150 is then advanced in a proximal direction away from the balloon 122, which causes the strings 121 and 131 to be pulled taut, and the eyelets 135 and 136 to be locked with the corresponding rings 105. This embodiment 15A and 15B operates under similar principles as the embodiments above, except that the middle sheath 150 is provided instead of a longer string 131.

The present invention provides a method and an assembly for effectively securing an implantable medical device to a delivery system for delivery to a treatment location, and for deployment of the implant at the treatment location, in a manner such that the medical device experiences minimal to no movement in its crimped position over the balloon. Providing the rings 105 at the opposing ends of the medical device, using the strings 121 and 131 to receive a locking wire 126 that is threaded through these rings 105, and covering the medical device with a sheath, together locks the medical device on the deflated balloon and prevents flaring of the ends of the medical device, and thereby minimizes the risks of piercing the balloon.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:
1. A method of securing a crimped medical device over a deflated balloon of a balloon catheter, comprising the steps of:
   providing a medical device having a tubular device body that has a first end and a second end, with a first ring provided at the first end and a second ring provided at the second end;
   providing a balloon catheter having a catheter body that has a distal tip, and a balloon provided adjacent to, and proximal to, the distal tip, and having a distal end and a proximal end, the balloon catheter further including a first string secured to the balloon catheter at a position adjacent the distal end of the balloon and having a first eyelet, and a second string secured to the balloon catheter at a position adjacent the proximal end of the balloon and having a second eyelet;
   providing a sheath for sliding movement over the catheter body and the balloon, the sheath having a distal end;
   positioning the medical device in its expanded state over the deflated balloon;
   crimping the medical device over the deflated balloon;
   threading the first and second eyelets of the first and second strings, respectively, through the first and second rings, respectively;
   advancing a locking wire through the first and second eyelets and into the distal tip; and
   advancing the sheath over the crimped medical device to the distal tip to completely cover the crimped medical device; and the method further including providing a connecting wire that connects the first and second strings; and the method further including providing a central lumen extending through the balloon, and wherein the connecting wire extends through the central lumen.

2. The method of claim 1, wherein the step of advancing a locking wire includes the step of advancing the locking wire through a lumen defined between the sheath and the catheter body to exit the distal end of the sheath.

3. The method of claim 1, wherein the step of threading the first and second eyelets includes the step of locking each of the first and second eyelets at the first and second rings, respectively.

4. The method of claim 1, wherein each of the first and second rings is provided as an independent ring and attached to the first and second ends, respectively, of the medical device.

5. The method of claim 1, wherein each of the first and second rings is provided as a rounded tip at the first and second ends, respectively, of the medical device.

6. The method of claim 1, wherein each of the first and second rings is provided as an opening in an apex at the first and second ends, respectively, of the medical device.

7. The method of claim 1, further including providing a middle sheath that extends through a lumen defined between the sheath and the catheter body, with the second string attached to a distal end of the middle sheath.

8. A method of implanting a medical device at a location in a human anatomy, wherein the medical device has been secured to a deflated balloon of a balloon catheter according to the method of claim 1, comprising the steps of:
- withdrawing the sheath in a proximal direction to expose the medical device;
- withdrawing the locking wire in a proximal direction;
- expanding the balloon, with the expanding balloon causing the first and second strings to be withdrawn through the first and second rings, respectively;
- deflating the balloon; and
- withdrawing the balloon catheter in a proximal direction.

* * * * *